United States Patent [19]

Ashihara et al.

[11] Patent Number: 4,692,404

[45] Date of Patent: * Sep. 8, 1987

[54] METHOD OF MEASURING BIOLOGICAL LIGAND BY THE USE OF ENZYMES

[75] Inventors: Yoshihiro Ashihara; Yasushi Kasahara, both of Tokyo, Japan

[73] Assignee: Fujirebio Kabushiki Kaisha, Tokyo, Japan

[ * ] Notice: The portion of the term of this patent subsequent to Nov. 4, 2003 has been disclaimed.

[21] Appl. No.: 670,764

[22] Filed: Nov. 13, 1984

[30] Foreign Application Priority Data

Nov. 18, 1983 [JP] Japan ................ 58-217145
Dec. 9, 1983 [JP] Japan ................ 58-231241

[51] Int. Cl.$^4$ .................. C12Q 1/34; C12Q 1/40; G01N 33/536
[52] U.S. Cl. .................. 435/5; 435/7; 435/18; 435/19; 435/22; 435/23; 436/512; 436/537; 436/548; 436/813; 436/815
[58] Field of Search ............ 435/5, 7, 18, 19, 22, 435/23; 436/512, 537, 548

[56] References Cited

U.S. PATENT DOCUMENTS 4,268,663  5/1981  Skold ................ 435/7
4,323,647  4/1982  Monji ................ 435/7

FOREIGN PATENT DOCUMENTS 0088974  9/1983  European Pat. Off. .

OTHER PUBLICATIONS

I. Gibbons et al. *Anal. Biochem.* 102, 167–170, 1980.
R. H. Yolken, *Rev. Infect. Diseases* 4, 35–68, 1982.
*Worthington Enzyme Manual*, Worthington Biochemical Corporation, Freehold, N.J. 1972, pp. 63–64, 96–97, 132–133, 138–140.

Primary Examiner—Robert J. Warden
Assistant Examiner—David A. Saunders
Attorney, Agent, or Firm—Burgess, Ryan and Wayne

[57] ABSTRACT

A method is provided which is highly sensitive and specific, and is suitable as a clinical test for the determination of physiological substances and trace components in humoral fluid. The method employs a conjugate of an enzyme capable of acting on a water-insoluble macromolecular substance and an antibody against the ligand (1) to be measured or a ligand (2) having an antigenic determinant common to one of the antigenic determinant(s) of the ligand (1). In the method of the invention, steric hindrance of the conjugate is emphasized by the enzyme reaction which is carried out at the boundary between solid phase and liquid phase.

14 Claims, 5 Drawing Figures

4,692,404

METHOD OF MEASURING BIOLOGICAL LIGAND BY THE USE OF ENZYMES

FIELD OF THE INVENTION

The measurement of the concentration in the blood of a drug administered to a patient is important in the treatment of various diseases. Additionally, the detection of trace components derived from various diseases in the blood of a patient is also important in early diagnosis of the diseases. Accordingly, this invention relates to a method of measuring a biological ligand including medicinal substances and trace components derived from various diseases.

BACKGROUND OF THE INVENTION

A humoral fluid such as blood contains various components, some of which are similar to each other in their molecular weights or physiological properties. Accordingly, the measurement of such components requires high specificity and high sensitivity. Furthermore, in order to evaluate various components for diagnosis of a disease, the measuring procedure must of necessity be simple.

Various methods to detect trace components in blood have been developed, among them enzyme immunoassay which is widely employed because of its sensitivity, specificity and ability to process a large number of samples. However, in the case of conventional enzyme immunoassay, the sensitivity is not always adequate and it is not easy to obtain an exact concentration because of the complicated washing procedures and the transferring of tubes.

Various enzyme immunoassays using conjugates of a ligand or an antibody and an enzyme or a material having an enzyme inhibitory activity have been reported in the literature.

For example in Japanese Patent Application 142466/1982 a method of measuring a biological ligand was reported which comprises, contacting a ligand (1) to be measured with a conjugate of a ligand (2) having an antigenic determinant common to one of the antigenic determinant(s) of the above ligand (1) and biotin or its derivatives capable of reacting with avidin or streptoavidin with an antibody capable of reacting with the above common antigenic determinant in an aqueous solution. Thereafter contacting the above conjugate with avidin, streptoavidin or one of their derivatives capable of reacting with biotin, and measuring the biotin enzyme activity.

Also known is a method of measuring a biological ligand which comprises, contacting a ligand to be measured and an enzyme or a conjugate of an enzyme and a macromolecular substance, with a conjugate of an antibody against the above ligand and an antibody against the above enzyme, or with a conjugate of an antibody against the above ligand, an antibody against the above enzyme and a macromolecular substance in an aqueous solution, and measuring the activity of the enzyme.

Another method of measuring a biological ligand is known in the literature which comprises, allowing to coexist a biologically active composition comprising an immobilization phase of an antibody capable of reacting with the ligand (1) to be measured or a biological ligand (2) capable of reacting with the above antibody and an immobilization phase of a biotin-containing enzyme or a biotin-containing enzyme inhibitor, a water-soluble conjugate of the above ligand (2) or the above antibody and a biotin-containing enzyme inhibitor capable of reacting with the above biotin-containing enzyme or a biotinyl enzyme capable of reacting with the above biotin-containing enzyme inhibitor, and the ligand (1) to be measured in an aqueous solution, and measuring the biotin-containing enzyme activity or the biotinyl enzyme inhibitory activity of the biologically active composition or the aqueous solution.

Also known is a method of measuring a biological ligand which comprises, contacting a ligand (1) to be measured and a conjugate of a ligand (2) having an antigenic determinant being common to one of the antigenic determinant(s) of the ligand (1) and a biotin-containing enzyme inhibitor with an antibody capable of reacting with the common antigenic determinant in an aqueous solution, contacting the above combination with a biotin-containing enzyme, and measuring the biotin-containing enzyme activity.

SUMMARY OF THE INVENTION

It has now been found that when a conjugate of an enzyme capable of acting on a water-insoluble micromolecular substance and a ligand or an antibody is employed as the conjugate hereinafter described, the ligand in a sample can be detected with a high degree of sensitivity and the procedure is also simplified.

The method of the invention comprises, using an antibody or ligand binding fragments thereof against the ligand (1) to be measured and an enzyme capable of acting on a water-insoluble macromolecular substance which conjugate with the antibody or with a ligand (2) having an antigenic determinant common to one of the antigenic determinant(s) of the ligand (1), allowing the antibody or ligand binding fragments thereof to contact the ligand(s), allowing the enzyme to contact the macromolecular substance, and thereafter measuring the concentration of the ligand.

DETAILED DESCRIPTION OF THE INVENTION

Figure 1:
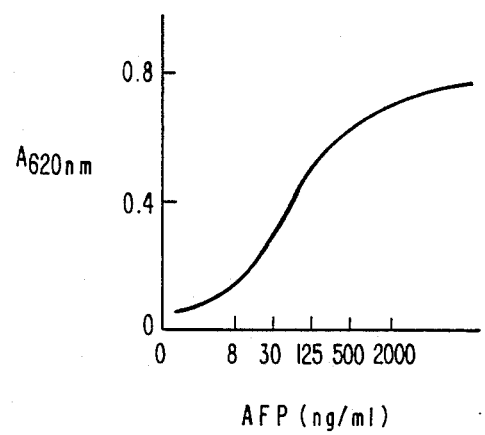
FIG. 1 shows the relationship between the concentration of α-fetoprotein and the absorbance measured in an enzyme immunoassay.

The subject to be measured by the method of the invention is a ligand (1). The ligand (1) is a substance having one or more antigenic determinants, and includes, for example, hormones derived from various endocrine glands, plasma proteins such as immunoglobulin, albumin and ferritin, viral antigens such as HB antigen, bacteria, α-fetoprotein, and carcinoembryonic antigens. The ligand (1) also includes a hapten and a first antibody in the double antibody method. The ligand (1)

includes, for example, the conjugate of the desired antigen to be measured and a first antibody in the case of the double antibody method. Samples containing ligand (1) are not limited, and includes serum and urine.

The ligand (2) also has one or more antigenic determinants and at least one antigenic determinant is common to one of the antigenic determinant(s) of the ligand (1). All antigenic determinants of the ligand (2) may be equal to those of the ligand (1), and accordingly, ligand (2) may be identical with the ligand (1).

The antibody should be the antibody against this common antigenic determinant. The antibody includes fragments of immunoglobulin such as F(ab')$_2$, Fab' and Fab.

Such an antibody may be produced according to known methods of producing an antibody. For example, the ligand (1), the ligand (2) or a conjugate of either of these ligand and a protein material is injected once or several times into the subcutaneous region of the back, foot pad or femoral muscle of a warm-blooded animal such as a rabbit, goat, horse, guinea pig and chicken, in an amount of about 0.3 to 2 mg per kg together with an adjuvant, thereby producing the antibody in the humoral fluid such as serum. This humoral fluid, as it is, may be used as the antibody, however, the antibody may preferably be separated according to a conventional isolation method of an immunoglobulin.

On the other hand, the antibody may be produced as a monoclonal antibody. In this case, one of the above antigens is injected several times into the abdominal cavity of a mouse together with an adjuvant, and its spleen is excised. The spleen cell is fused with a mouse myeloma cell by a conventional method involving the use of polyethylene glycol. The hybridoma thus obtained is cultured and cloned, and the cell capable of producing the desired antibody is obtained. This cell is injected into the abdominal cavity of a mouse, and multiplied. Then, ascites are collected, and the desired antibody is separated from the ascites.

In the case where the antibody does not conjugate with the enzyme described later, if the enzyme activity does not appreciably vary through the reaction of the antibody with the ligand (2) portion of the conjugate which is also described later, a macromolecular compound may preferably be conjugated to the antibody prior to use. Preferred macromolecular compounds are water-soluble, and their molecular weights are greater than about 100,000 daltons. Examples of the macromolecular compounds include polysaccharides and their derivatives such as soluble dextran, carboxymethyl dextran, dextran into which amino groups have been introduced and amylose, proteins such as gelatin, hemocyanin and ferritin, and polyethylene glycol. The macromolecular compound may be conjugated to the antibody according to the conjugation method described later.

The enzyme is able to act on a water-insoluble macromolecular substance. Enzymes whose activities are easily measured are preferred. Examples of such enzymes include α-amylase, cellulase, collagenase, mannase, protease, elastase, lipase and the like.

The enzyme is allowed to conjugate with the antibody or the ligand (2). When it is allowed to conjugate with the antibody, the ligand (2) is not used. On the other hand, when it is allowed to conjugate with the ligand (2), the antibody is used in its natural form or conjugated with a macromolecular compound.

The conjugation method of the enzyme and the antibody or the ligand (2) may be selected by considering the functional groups of both substances. Such functional groups include, amino groups, carboxyl groups, hydroxyl groups, thiol groups, imidazole groups, phenyl groups, and the like. the introduction of amino groups, may be carried out by many methods such as the diisocyanate method, the glutaraldehyde method, the difluorobenzene method, the benzoquinone method, and the like. As the method to introduce an amino group and a carboxyl group, the peptide-binding method of carboxyl group to succinimide ester, the carbodiimide method, the Woodward reagent method are known. The periodate oxidation method (Nakane method) where a bridge between amino group and sugar chain forms is also utilized. In the case of using a thiol group, for example, a carboxyl group is first converted to a succinimide ester, and this ester group is then allowed to react with cysteine to introduce the thiol group, and both thiol groups are introduced by using a thiol-reactive bifunctional cross-linking reagent such as phenylene-bismaleimide. As the method of utilizing a phenyl group, the diazotization method and the alkylation method are utilized. Other than the above, a suitable method may be selected from the various methods described in "Method in Immunology and Immunochemistry" (C. A. Williams et al., 1976, Academic Press N.Y.) and "Koso Meneki Sokutei-ho" (E. Ishikawa et al., 1978, Igakuashoin (Japan)). The molar ratio of the conjugate is not limited to 1:1, and suitable ratios can be easily selected. After the binding reaction, the conjugate produced is purified by gel filtration, ion-exchange chromatography and affinity chromatography, and lyophilized, if necessary.

When the enzyme conjugates with the antibody, the antibody is allowed to contact the ligand (1) to be measured. While, when the enzyme conjugates with the ligand (2), the antibody is allowed to contact the ligand (1) and the ligand (2) portion of the conjugate. In the latter case, the order of the contacting is not limited, and either of the ligand (1) and the conjugate may first be allowed to contact with the antibody. Of course, both materials may be allowed to contact at the same time. The temperature of the solution is usually kept at about 20° to 45° C., and the pH is usually kept at about 4 to 8.5. In order to keep the pH constant, a buffer solution such as a phosphate buffer solution and an acetate buffer solution may be employed. Since the suitable amounts of the conjugate and the antibody are different according to their kinds, the kind of the ligand (1), the contacting conditions and the like, the amounts may preferably be determined by a preliminary test.

In the case that the antibody does not conjugate with the enzyme, if the enzyme activity does not appreciably vary through the reaction of the antibody with the ligand (2) portion of the conjugate, a second antibody may further be allowed to react with the antibody conjugated to the ligand (2) portion. The second antibody may be prepared according to the same method as previously described.

Subsequently, the conjugate is allowed to contact a water-insoluble macromolecular substance. The conjugate may usually be in the reaction solution, or it may also be separated.

The macromolecular substance is able to react by the action of the enzyme, and it is usually a substrate of the enzyme. The macromolecular substance is characterized by its insolubility in water. That is, most of the contacting of the macromolecular substance with the enzyme portion of the conjugate is carried out at the boundary between solid and solution, and as the result, steric hindrance of macromolecule(s) conjugated to the enzyme largely appears. This matter is supported by the experiment carried out where a pentaose and an insoluble starch were digested by an α-amylase which was in its natural form or which was previously allowed to conjugate with a macromolecule. As the results of the experiment, the enzyme activity was scarcely lowered by the conjugation of the macromolecule in the case of the pentaose, while it was remarkably lowered in the case of the insoluble starch. The macromolecular substances include insoluble starches in the case of α-amylase, celluloses in the case of cellulase, collagen in the case of collagenase, mannan in the case of mannase, insoluble proteins in the case of protease, elastin in the case of elastase, and various lipids in the case of lipase. When the macromolecular substance is water-soluble, it may also be used by the insolubilization of this substance. The insolubilization may be carried out by the conjugation with an insoluble carrier material or by the polymerization of itself.

The conditions of the enzyme reaction may be determined according to the enzyme employed.

After the reaction, the enzyme activity is determined by detecting the changes of the reaction mixture, such as the increase of a decomposition product, the decrease of the raw material, and the like.

According to the method of the invention, a biological ligand can be detected and determined in high sensitivity and in high specificity. The operation of this method is simple, and a biological ligand can easily and inexpensively be determined. The kind of the ligand to be measured is not limited, and the present method is suitable for the measurement of a ligand having a relatively high molecular weight. In the case where the conjugate of the antibody and the enzyme are employed since the ligand is used only as the antigen which is necessary to produce the antibody, the amount of the ligand can be very small. Accordingly, when only small amount of the ligand can be obtained and when the ligand is extremely expensive, this method is particularly effective.

EXAMPLE 1

(i) Preparation of Cellulase Substrate

A filter paper was cut into a piece having the size of 20 cm × 20 cm. The piece was immersed in a reactive blue solution (prepared by dissolving 5 g of reactive blue and 5 g of $Na_2CO_3$ in 200 ml of distilled water), and kept at 60° C. for 3 days with occasional stirring. The filter paper was sufficiently washed with distilled water to remove the excess dye. Subsequently, the filter paper was dried in a dryer having a thermostat, and cut into pieces of size 1 cm × 5 cm to obtain the object substrate.

(ii) Preparation of Conjugate of Cellulase and Human IgG 10 mg of cellulase was dissolved in 2 ml of 0.1M phosphate buffer solution pH 6.0, and 200 μl of 2 mg/ml 4-maleimidomethyl cyclohexane-1-carboxylic acid succinimide ester (CHMS) dimethyl sulfoxide solution was added. The mixture was allowed to stand at room temperature for one hour. Gel filtration using SEPHADEX G-25, a cross-linked polysaccharide was carried out and unreacted CHMS was removed from the reaction mixture. Then, it was concentrated to 1 ml to obtain CHMS-introduced cellulase.

Thereafter, 10 mg of human IgG was dissolved in 2 ml of 0.1M phosphate buffer solution pH 7.5. 200 μl of 9 mg/ml S-acetylmercaptosuccinic anhydride (SAMS) dioxane solution was added to this, and allowed to stand at 37° C. for 1 hour. Subsequently, 200 μl of 1M hydroxylamine aqueous solution pH 7.5 was added, and allowed to stand at 37° C. for 30 minutes. Gel filtration using SEPHADEX G-25 was carried out, and unreacted SAMS was removed from the reaction mixture. HS-human IgG solution thus obtained was added to 1 ml of the above CHMS-introduced cellulase, and allowed to stand at 37° C. for 2 hours. The reaction mixture was separated by gel filtration using SEPHACRYL S-300, a cross-linked polysaccharide, and the desired conjugate of cellulase and human IgG was obtained.

(iii) Measurement of Human IgG

50 μl of a standard solution containing human IgG was added to 50 μl of a solution containing the above conjugate. 5 μl of anti-human IgG goat serum was added to this mixture, and allowed to stand at 37° C. for 1 hour. 1 ml of 0.1M acetate buffer solution pH 5.0 was added to this, and one piece of the blue cellulose filter paper prepared in item (1) was then added. After 1 hour, the absorbance at 620 nm of the reaction solution was measured. The relation between the human IgG concentration and the absorbance is shown in the following table.

| Human IgG (μg) | $\Delta A_{620\ nm}$ |
| --- | --- |
| 0 | 0.280 |
| 100 | 0.380 |
| 200 | 0.490 |
| 400 | 0.630 |
| 800 | 0.990 |
| 2000 | 1.220 |

EXAMPLE 2

(i) Preparation of CHM-introduced Amylase 5 mg of Bacillus subtilis amylase was dissolved in 1 ml of 0.1M phosphate buffer solution pH 6.3. 100 μl of 2 mg/ml CHMS dimethylformamide (DMF) solution was added to this, and allowed to stand at room temperature for 1 hour. The reaction mixture was introduced into a SEPHADEX G-25 column, and gel filtration was carried out by using 0.1M phosphate buffer solution pH 6.3. The void fractions were collected to obtain the object CHM-introduced amylase.

(ii) Preparation of SH-introduced-Fetoprotein 5 mg of α-fetoprotein was dissolved in 0.1M phosphate buffer solution containing 5 mM EDTA. 100 μl of 9 mg/ml SAMS DMF solution was added to this, and allowed to react at 37° C. for 1 hour. 110 μl of 1M hydroxylamine aqueous solution pH 7.5 was added to the reaction mixture, and allowed to warm at 37° C. for 30 minutes. Subsequently, gel filtration using SEPHADEX G-25 was carried out as to the reaction mixture, and the void fractions were collected to obtain the object SH-introduced α-fetoprotein.

(iii) Preparation of Conjugate of Amylase and α-Fetoprotein

The above CHM-introduced amylase solution was mixed with the SH-introduced α-fetoprotein solution. The mixture was concentrated to 1 ml, and allowed to react at 4° C. overnight. The reaction solution was introduced into a SEPHACRYL S-300 column, and gel filtration was carried out by using 20 mM phosphate buffered saline solution pH 7.0. The fractions containing the conjugates of which molar ratio was 1:1 were collected.

(iv) Measurement of α-Fetoprotein

Each 50 μl of an α-fetoprotein solution of which concentration was in the range of 0–2000 ng was mixed with 50 μl of the conjugate solution prepared in the above item (iii). 50 μl of 8 μg/ml anti-α-fetoprotein goat IgG solution was added to each mixture, and allowed to react for 20 minutes. 1.0 ml of blue starch (made by Pharmacia, Diagnostics, A.B.) suspension was added to reaction mixture, and allowed to react at 37° C. for 20 minutes. The enzyme reaction was terminated by adding 1 ml of 0.5N NaOH. The mixture was stirred, and then centrifuged at 3,500 rpm for 2 minutes. The absorbance at 620 nm of the supernatant was measured. The relation between the α-fetoprotein concentration and the absorbance thus obtained is shown in FIG. 1.

EXAMPLE 3

5 mg of α-amylase was dissolved in 1 ml of 0.1M carbonate buffer solution pH 8.0. 100 μl of 20 μg/ml 3-carboxytheophylline succinimide ester DMF solution was added to this, and allowed to react at room temperature for 1 hour. Gel filtration using SEPHADEX G-25 column which was previously equilibrated with 20 mM phosphate buffered saline solution pH 6.5 containing 20 mM calcium chloride was carried out, and the void fractions was collected. The fractions were concentrated to 1 ml to obtain the conjugate of theophylline and α-amylase.

Figure 2:
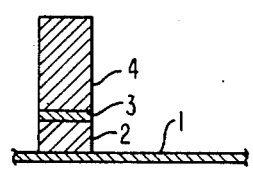
FIG. 2 shows a laminate film consisting of a polystyrene film 1, a cation-exchange resin layer 2, a reflection layer 3 and blue starch layer 4.
Figure 3:
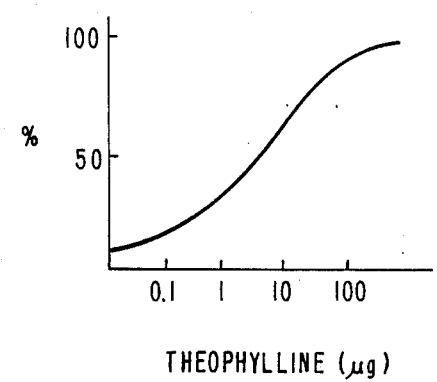
FIG. 3 shows the relationship between theophyline concentration and the reflection intensity of the laminate film of FIG. 2.

50 μl of 800 ng/ml of this conjugate solution was added to 50 μl of serum, and in order to inhibit human serum amylase, 50 μl of 500 μg/ml anti-human amylase goat IgG was added to the mixture. 50 μl of 15 μg/ml anti-theophylline mouse IgG was further added, and allowed to react at 37° C. for 30 minutes. 100 μl of this reaction solution was dropped on a laminate film which consisted of polystyrene film 1, a cation-exchange resin layer 2, a reflection layer 3 and blue starch layer 4 as shown in FIG. 2. The amylase activity at room temperature after 20 minutes was measured by using a reflectometer. The relation between the theophylline concentration and the reflection intensity thus obtained is shown in FIG. 3.

EXAMPLE 4

(i) Preparation of Cellulase Substrate

Blue cellulose filter papers having the size of 1 cm × 5 cm were prepared in the same manner as described in item (i) of Example 1.

(ii) Preparation of Conjugate of Cellulase and Anti-Human IgG Goat IgG

CHMS-introduced cellulase 1 ml was prepared in the same manner as described in the front part of item (ii) of Example 1.

Thereafter, 10 ml of anti-human IgG goat IgG was dissolved in 2 ml of 0.1M phosphate buffer solution containing 5 mM EDTA. 200 μl of 9 mg/ml SAMS dioxane solution as added to this, and allowed to stand at 37° C. for 1 hour. 200 μl of 1M hydroxylamine aqueous solution pH 7.5 was added, and allowed to stand at 37° C. for 30 minutes. Gel filtration using SEPHADEX G-25 was carried out as to the reaction mixture, and unreacted SAMS was removed.

This HS-anti-human IgG goat IgG solution was added to 1 ml of the above CHM-introduced cellulase, and allowed to stand at 37° C. for 2 hours. The reaction mixture was separated by gel filtration using SEPHACRYL S-300, and the object conjugate of cellulase and anti-human IgG goat IgG was obtained.

(iii) Measurement of Human IgG

Figure 4:
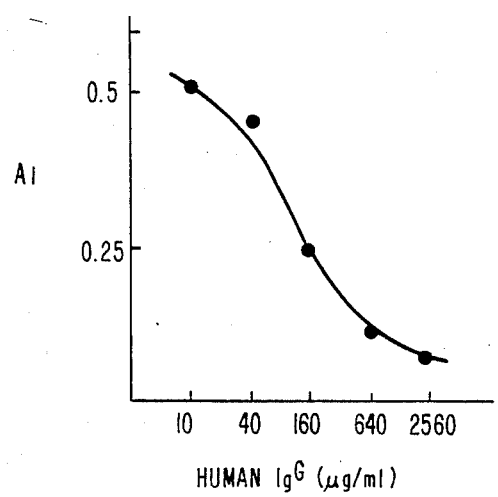
FIG. 4 shows the relationship, between the concentration of human IgG and the absorbance measured in an enzyme immunoassay.

50 μl of a standard solution containing human IgG was added to 50 μl of a solution containing the above conjugate of cellulase and anti-human IgG goat IgG, and allowed to stand at 37° C. for 30 minutes. 1 ml of 0.1M acetate buffer solution pH 5.0 was added, and one piece of the blue cellulose filter paper prepared in item (i) was then added. After 1 hour, the absorbance at 620 nm of the reaction solution was measured. The relation between the human IgG concentration and the absorbance is shown in FIG. 4.

EXAMPLE 5

(i) Preparation of CHM-introduced Amylase

CHM-introduced amylase was prepared from Bacillus subtilis amylase in the same manner as described in item (i) of Example 2.

(ii) Preparation of Anti-Human α-Fetoprotein Goat IgG F(ab')$_2$ 10 mg of anti-human α-fetoprotein goat IgG was dissolved in 2 ml of 0.1M acetate buffer solution pH 4.0. 300 μg of pepsin was added to this, and stirred at 37° C. for 18 hours. The solution was adjusted to pH 6.0 by adding 0.1N NaOH, and introduced into a SEPHACRYL S-300 column which was previously equilibrated with 0.1M phosphate buffered 1 mM EDTA solution pH 6.3, and eluted by the above phosphate buffer solution without EDTA. A peak fractions corresponding to the molecular weight of about 100,000 were collected, and concentrated to 1 ml to obtain the object anti-human α-fetroprotein goat IgG F(ab')$_2$.

(iii) Preparation Conjugate of Amylase and Anti-Human-Fetoprotein Goat IgG Fab'

1 ml of 0.1M phosphate buffered 1 mM EDTA solution pH 6.0 containing 6 mg of the above anti-human α-fetoprotein goat IgG F(ab')$_2$ was mixed with 100 μl of 10 mg/ml 2-mercaptoethylamine hydrochloride aqueous solution, and stirred at 37° C. for 90 minutes. Gel filtration using a SEPHADEX G-25 column which was previously equilibrated with 0.1M phosphate buffer solution pH 6.3 was carried out, and unreacted 2-mercaptoethylamine was removed to obtain HS-Fab'. 2 mg of CHM-introduced α-amylase prepared in item (i) was added, and allowed to react at 37° C. for 90 minutes. Subsequently, this reaction mixture was separated by gel filtration using a SEPHACRYL S-300 column which was equilibrated with 0.1M acetate buffered 5 mM calcium chloride solution pH 6.0, and the fractions corresponding to the molecular weights of greater than 200,000 were collected. The fractions were concentrated to obtain the object conjugate.

Figure 5:
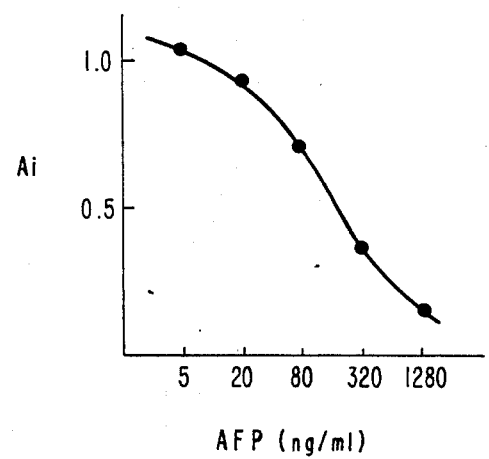
FIG. 5 shows the relationship between the concentration of α-fetoprotein and the absorbance measured in an enzyme immunoassay.

Each 50 μl of an α-fetoprotein solution of which concentration was in the range of 0–2000 ng was mixed with 50 μl of the conjugate solution prepared in the above item (iii), and allowed to react for 20 minutes. 1.0 ml of blue starch (made by Pharmacia Diagnostics, A.B.) suspension was added to the reaction mixture, and further allowed to react at 37° C. for 20 minutes. The enzyme reaction was terminated by adding 1 ml of 0.5N NaOH. The mixture was stirred, and then centrifuged at 3,500 rpm for 2 minutes. The absorbance at 620 nm of the supernatant was measured. The relation between the α-fetoprotein concentration and the absorbance thus obtained is shown in FIG. 5.

We claim:

1. A method of determining a biological ligand which comprises, using an antibody or ligand binding fragments thereof, against the ligand to be measured and an enzyme capable of acting on a water-insoluble macromolecular substrate and which conjugates with said antibody or ligand binding fragments thereof, contacting said antibody or ligand binding fragments thereof, with said ligand, contacting said enzyme with a water-insoluble macromolecular substrate, and thereafter measuring the change in activity of the enzyme after it has acted on said substrate, relating said change in the activity of the enzyme to the concentration of the ligand.

2. The method of claim 1, wherein said ligand (1) and said ligand (2) are the same.

3. A method of determining a biological ligand using an antibody or ligand binding fragment thereof against the ligand (1) to be measured and an enzyme capable of acting on a water-insoluble macromolecular substrate and which conjugates with a ligand (2) having an antigenic determinant common to one of the antigenic determinant(s) of said ligand (1), which method comprises:

contacting said antibody or ligand binding fragment thereof with said ligands (1) and (2), contacting said enzyme with a water-insoluble macromolecular substrate, and thereafter measuring the change in activity of the enzyme after it has acted on said substrate, relating said change in the activity of the enzyme to the concentration of the ligand (1).

4. The method of claim 1 or claim 3, wherein said antibody or ligand binding fragments thereof conjugates with a macromolecular compound which is water-soluble and which has a molecular weight greater than 100,000 daltons.

5. The method of claim 1 or claim 3, wherein said ligand is a member selected from the group consisting of hormones derived from endocrine glands, plasma proteins, viral antigens, bacteria, α-fetoprotein, and carcinoembryonic antigens.

6. The method of claim 1 or claim 3, wherein said antibody is a monoclonal antibody.

7. The method of claim 1 or claim 3, wherein said enzyme is a member selected from the group consisting of α-amylase, cellulase, collagenase, mannase, protease, elastase, and lipase.

8. The method of claim 7, wherein said macromolecular substance is insoluble starch and said enzyme is α-amylase.

9. The method of claim 7 wherein said macromolecular substance is cellulose and said enzyme is cellulase.

10. The method of claim 7 wherein saidmacromolecular substance is collagen and said enzyme is collagenase.

11. The method of claim 7 wherein said macromolecular substance is mannan and said enzyme is mannase.

12. The method of claim 7 wherein said macromolecular substance is an insoluble protein and said enzyme is protease.

13. The method of claim 7 wherein said macromolecular substance is elastin and said enzyme is elastase.

14. The method of claim 7 wherein said macromolecular substance is lipid and said enzyme is lipase.

* * * * *